United States Patent [19]

Milhous, Jr. et al.

[11] Patent Number: 4,589,775
[45] Date of Patent: May 20, 1986

[54] APPARATUS AND METHOD FOR ACCUMULATING AND MEASURING SIDESTREAM SMOKE PRODUCED BY A SMOKING MATERIAL

[75] Inventors: Leon A. Milhous, Jr.; John M. Martin; Clifton T. Mansfield, all of Winston-Salem, N.C.

[73] Assignee: R. J. Reynolds Tobacco Company, Winston-Salem, N.C.

[21] Appl. No.: 554,549

[22] Filed: Nov. 23, 1983

[51] Int. Cl.⁴ ............................................. G01N 21/00
[52] U.S. Cl. ..................................... 356/439; 356/440
[58] Field of Search ............... 356/433, 434, 437, 438, 356/439, 440

[56] References Cited

U.S. PATENT DOCUMENTS 4,021,713  5/1977  Suga ................................. 356/439 X
4,413,911 11/1983  Rice et al. .......................... 356/438

Primary Examiner—Michael R. Lusignan
Attorney, Agent, or Firm—Grover M. Myers

[57] ABSTRACT

Apparatus and method for collecting sidestream smoke produced by a cigarette is disclosed. The apparatus includes a chamber that has upper and lower portions between which smoke may freely move. A cigarette holder is attached to the lower portion so that substantially all of the sidestream smoke produced by the cigarette is released into the chamber means. Smoking means is connected to the cigarette holder means to intermittently draw air through the cigarette and segregate the mainstream smoke from the sidestream smoke. The total relative amount of sidestream smoke may be measured by measuring the opacity of the collected sidestream smoke.

26 Claims, 2 Drawing Figures

APPARATUS AND METHOD FOR ACCUMULATING AND MEASURING SIDESTREAM SMOKE PRODUCED BY A SMOKING MATERIAL

FIELD OF THE INVENTION

This invention relates to the accumulation and measurement of the relative amount of sidestream smoke produced by a smoking material such as a cigarette. The apparatus is configured to collect sidestream smoke only, apart from the mainstream smoke, and maintain it for a period of time, so that a relative measurement of the amount of sidestream smoke may be made.

BACKGROUND OF THE INVENTION

Over the years a number of methods and a variety of apparatus were developed to collect and analyze the mainstream smoke from a cigarette, but there was no simple and convenient apparatus to collect or analyze the sidestream smoke from a cigarette. Similarly, there was no method or apparatus to determine accurately the relative amount of sidestream smoke produced by a cigarette.

Pyrolysis of tobacco in a cigarette produces several resultant products, commonly lumped together as "smoke." One way to classify such products is to divide "sidestream smoke"—that which passes directly from the cigarette surface to the atmosphere—from "mainstream smoke"—that which is drawn lengthwise through the cigarette to the user by drawing a slight vacuum on the unlit end. Also, "smoke" consists of a mixture of constituents in both aerosol and gaseous form; the former is visible, and the latter is not, due to the size of the particles concerned. The present invention relates to the accumulation and measurement of the aerosol portion of the sidestream smoke, and the term "sidestream smoke" as used herein refers solely to that portion of cigarette pyrolysis products.

Source emission monitors are well known and used in industrial facilities to measure smokestack emissions from factories. However, the apparatus and methodology used therein are not suitable for the collection and measurement of sidestream cigarette smoke because of the differences in size and complexity, the nature of the emissions measured, the environment in which measurements are made, the necessity of distinguishing among different emissions, and the relatively constant rate at which emissions are produced. In addition, source emission monitors relate to making absolute measurements of the amount of emissions on a continuing and instantaneous basis. Such monitors may measure opacity or gaseous emissions, and each type must meet rigid performance standards to provide an accurate, absolute reading.

The present invention may be generally classified as measuring opacity, but because it provides relative measurements rather than absolute measurements, it is simple in design and operation, inexpensive, very reliable, and easy to operate and maintain. In general, opacity monitors measure the attenuation of a light beam traveling from a source to a light sensor at a remote point, with the attenuation of the light beam being primarily due to absorption or scattering of the light by the matter between the source and sensor. Light carries energy, and will therefore interact with any particles, such as smoke particles, that it may strike, as energy from the light is absorbed by the particles. Moreover, different colors of light have different wavelengths and will have different effects upon different particles in terms of transferring energy thereto. Low energy light, i.e. light having a long wavelength, may cause a molecule to rotate. Light of a higher energy may cause a molecule to vibrate, and light of a still higher energy may excite an electron in the molecule to jump into a new orbit. Accordingly, one must accurately control the wavelength of the light source or compensate for the vagaries of energy absorbtion to obtain absolute measurements of the properties of the measured aerosol.

The opacity of an aerosol is also a function of light scattering. For particles having a diameter of the same order of magnitude of a wavelength of light or larger, scattering may be by way of external reflection, refraction, internal reflection, or diffraction. Each of these may have a different effect, and there may also be different cumulative effects. Particles having a diameter substantially smaller than a wavelength of light will scatter light by a process referred to as dipole or Rayleigh scattering, which causes the electrons in the molecule to oscillate. The oscillating electron will radiate energy in all directions, which scatters light in all directions. Due to the differences in the way that different size molecules scatter different wavelengths of light, these phenomenon can become very important in studying the opacity of an aerosol.

These principles relating to the attenuation of light have been used to design transmissometers, which monitor the concentration of particles emitted from smokestacks or the like. A transmissometer measures opacity by projecting a beam of light across a smokestack and the amount of light transmitted therethrough is a measure of the opacity of the emitted aerosol. It provides a quantitative value related to the decrease of the transmitted light, and, in the past, has provided an absolute value proportional to the percent opacity of the aerosol.

Prior art transmissometers have usually been very complex. To insure their accuracy, specific design criteria have included limitations on spectral output or composition of the light beam, angle of observation of the photodetector assembly, calibration error, response time, frequency of sampling, and systems operational checks. These criteria were deemed necessary because there is no widely available independent method of checking the opacity of the aerosol.

Aerosol monitors which utilize light for measurement rely upon the Beer-Lambert law. It states that the transmittance of light through a medium that absorbs or scatters light is decreased exponentially by the product $\alpha cl$, or $$T = I/I_o = e^{-\alpha cl}$$

where:
 $T$ = transmittance of light through the aerosol.
 $I$ = intensity of the light energy entering the aerosol.
 $I_o$ = intensity of the light energy leaving the aerosol.
 $\alpha$ = attenuation coefficient.
 $c$ = concentration of particles in the aerosol.
 $l$ = distance the light beam travels through the aerosol.

Opacity is related to transmittance as $100\%(1-T) = \%$ opacity.

The design principles and techniques utilized with transmissometers were tested for measurement of the amount of sidestream smoke produced by a cigarette, but there were multiple problems and they were unsuccessful. For instance, a tungsten halogen light source had its light beam focused across a chimney to a photodetector. Sidestream smoke from a cigarette was permitted to rise through the chimney, and measurements were taken. The results were erratic and inconclusive due to the lack of concentration of sidestream smoke, wandering of the sidestream smoke out of the light beam, background "noise" being a significant portion of the output signal, and spiking of the output during puffs on the cigarette. The present invention solved these problems with the apparatus and methods disclosed herein, which collects substantially all of the sidestream smoke produced by a cigarette and measures the total amount thereof. The apparatus and method are simplified by making relative measurements rather than absolute ones, which essentially holds constant several of the factors that might otherwise adversely affect an absolute measurement.

SUMMARY OF THE INVENTION

Thus, it is an object of the present invention to provide a novel apparatus and method for collecting and measuring sidestream smoke produced by a cigarette.

It is a further object of the present invention to provide a practical and simple apparatus for collecting and measuring the amount of sidestream smoke produced by a cigarette.

It is a still further object of the present invention to provide an apparatus and method for making relative measurements of the amount of sidestream smoke produced by a cigarette.

Further and additional objects will appear from the description, accompanying drawings, and appended claims.

In accordance with an embodiment of the invention, apparatus for collecting sidestream smoke produced by a cigarette is provided. It includes a substantially air tight chamber having upper and lower portions that are connected so that smoke may move freely between them. Cigarette holder means are attached to the lower portion of the chamber so that substantially all of the sidestream smoke from a cigarette held thereby is released within the chamber. Smoking means is connected to the cigarette holder to intermittently draw air through the cigarette to obtain mainstream smoke, which is prevented from comingling with said sidestream smoke. The opacity of the sidestream smoke is determined with a light transmitter and receiver which together measure the attenuation of a light beam directed through the sidestream smoke.

A method for collecting the sidestream smoke produced by a cigarette includes providing apparatus having a chamber with upper and lower portions, and a cigarette holder in the lower portion. A cigarette is placed into the cigarette holder and smoked, and the mainstream smoke produced thereby is segregated from the sidestream smoke. The sidestream smoke is accumulated and collected in the chamber upper portion. The relative amount of sidestream smoke may be determined by measuring its optical opacity.

DESCRIPTION OF THE INVENTION

Figure 1:
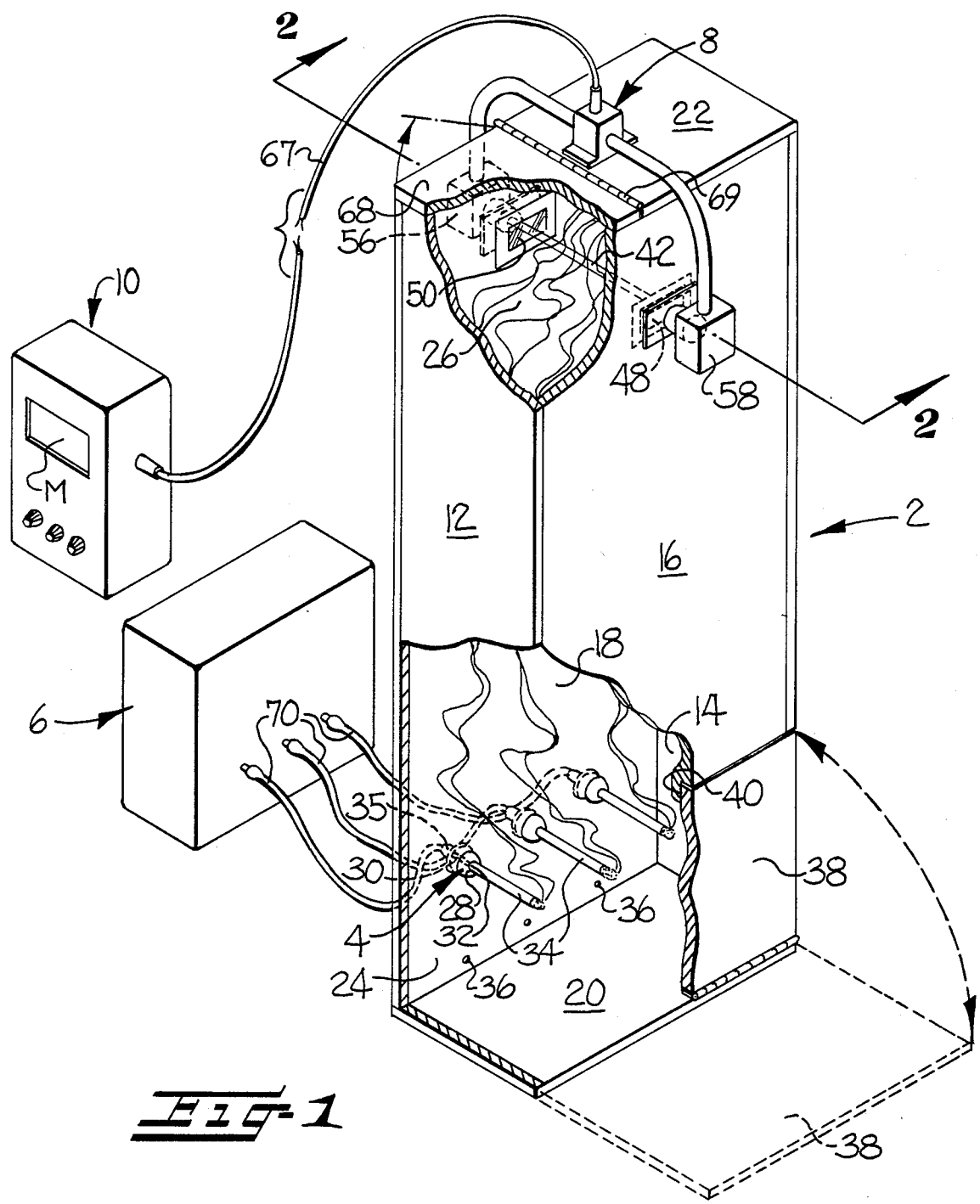
FIG. 1 is a perspective view of the apparatus of the present invention, with portions thereof cut away to show the interior thereof.

Referring to FIG. 1, the apparatus of the present invention generally includes a chamber means 2, cigarette holder means 4, and smoking means 6. It may additionally include an opacity measuring means 8, and any associated control circuitry 10.

Figure 2:
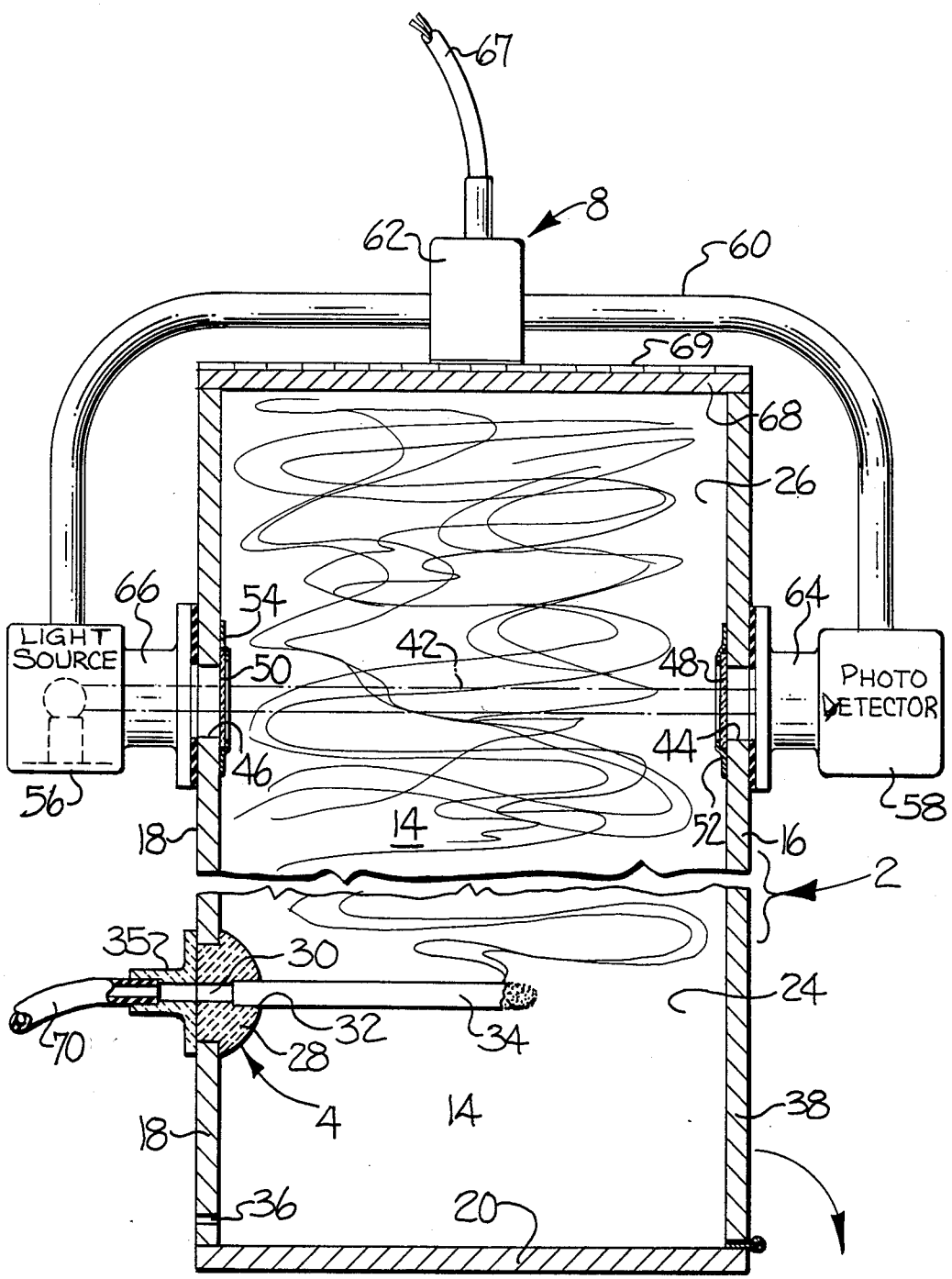
FIG. 2 is a cross sectional view of the upper portion of the apparatus of FIG. 1, taken along line 2—2.

Referring to FIGS. 1 and 2, and using like numerals to designate like items, a chamber means 2 is a generally closed box constructed of any suitable material, such as clear plastic-like sheet material. The chamber is illustrated as a rectangular prism, having pairs of opposing parallel side walls 12, 14 and 16, 18, but the shape is a matter of convenience and may be varied as desired consistent with the attributes noted herein. The chamber means 2 functions as a conduit and is closed on each end by cap segments 20, 22, to form a closed, generally air tight box. The chamber means includes a lower portion 24 and an upper portion 26 that are contiguous and connected so that smoke or any other gaseous or aerosol matter may move freely between them. Suitable dimensions are approximately 6 inches by 11 inches, with a height of 29 inches.

The lower portion 24 includes one or more cigarette holders 4 attached to rear wall 18 of the chamber means 2. Each cigarette holder generally comprises an annular collar 28 defining a port 30 therethrough. The collar is attached to the rear wall to form an air tight seal therewith. The port has a first end 32 disposed within the chamber means to releasably retain and support one end of a cigarette 34 or the like. A second end 35 of the port is disposed outside of the chamber means and is in communication with the first end of the port so that mainstream smoke from the cigarette 34 may be drawn therethrough. It is to be understood that references herein to a cigarette include any generally tubular product that may be smoked, including cigars. It is not limited to tubular products, as bulk items may be ground and placed on a screen disposed in a funnel. Mainstream smoke may be drawn through the funnel neck and connected to the first end 32 of the cigarette holder, and sidestream smoke may rise from the funnel mouth. The configuration of the cigarette holders may vary provided they make it possible to segregate the mainstream smoke from the sidestream smoke. Also, the number of cigarette holders is discretionary, with two or three being acceptable.

The cigarette holders are superposed a predetermined distance above the bottom cap 20. Approximately four inches from the bottom is acceptable.

A number of small apertures 36, approximately ⅛" in diameter and approximately one for each cigarette holder, are defined by one or more of the walls 12, 14, 16, 18 of the chamber 2. Each aperture connects the interior of the chamber to the oustide and functions as a vent. Each admits exterior air to support combustion and to maintain smoking characteristics that are consistent with mainstream smoke analysis or to simulate smoking by a person. If desired, the vents may be connected to a controlled or purified air source to avoid contamination of the chamber interior. However, this has been found unnecessary for the present invention.

An access door 38 may be incorporated into one or more of the chamber walls 12, 14, 16, 18. Its dimensions and location may vary, but for convenience it is located across from the cigarette holders 4 for ease of access thereto. It may further be hinged for ease of operation and preferably has an airtight seal around the edges where it mates with the adjacent wall or walls.

The upper portion 26 of the chamber 2 is illustrated in FIGS. 1 and 2, and it includes an optical path 42 extending thereacross. The optical path is defined by a pair of openings 44, 46 in opposite sidewalls 16, 18 that are transparent to light. A glass plate 48, 50 or the like is placed over each opening 44, 46 in air tight relation with the surrounding wall 16, 18 and releasably maintained in place by suitable clip means 52, 54 or the like. This provides an unobstructed path for a beam of light, yet prevents the passage of smoke therethrough. A suitable distance between the top cap 22, and the openings 44, 46 is approximately four inches.

A light source or light transmitter 56 and a complementary photo detector or light sensor 58 are disposed to transmit and detect light along the optical path 42. Such an opacity meter measures the attenuation of the light traversing the optical path. The light source and photodetector may be mounted on a single connecting yoke 60 that bridges the uppermost portion of the chamber means. The yoke insures proper spacing and alignment of the light source and photodetector, and may assist in positioning them with respect to the chamber means, as by a block 62 or the like. Depending upon the sensitivity of the photo detector to ambient light or other interference, or the necessity to focus the light source, each may be disposed as necessary or desirable with respect to its respective opening, and each may include an optional light-tight boot 64 or lenses 66 to optimize performance. A suitable opacity meter is Model P-6P manufactured and made commercially available by Wager. The light source is a green gallium phosphide light emitting diode and the photo detector is a silicon photodiode. This opacity meter meets all EPA standards for visible smoke monitoring and is not affected by ambient light. The control circuitry 10, connected to the light source and photo detector by wires 67, governs operation of the light source and photo detector, and displays the results as percent opacity on the meter M, or in digital form, as desired. It is to be understood that a variety of other photosensitive units and configurations may be used.

The upper cap 22 forms a generally air tight seal, and may include a portion 68 operably connected by a hinge 69 that may be opened to evacuate the chamber. This may further assist in cleaning the glass 48, 50.

The smoking machine 6 is typically capable of pulling, on a repeating basis, a predetermined amount of air or vacuum for a predetermined time, such as 35 cubic centimeters of air in 2 seconds, once every minute. These machines are well known and their workings need not be described further. The smoking machine includes at least one nozzle through which the vacuum is drawn. The nozzle is connected to a flexible tubing 70 or the like, which has its other end connected to the second end 35 of the cigarette holder 4.

To practice the method of the present invention, one uses an apparatus similar to that disclosed above. Initial adjustments are made to the smoking machine 6 so that it will pull the desired puff volume per period of time at the desired rate. Initial adjustments are also made to the opacity measuring means 8 to establish clear or no-smoke readings. For instance, the smoke opacity meter is adjusted for a clear chamber reading of 100% transmittance and an opaque reading for no transmittance. Assuming that the glass windows 48, 50 remain clear throughout the course of the experiments, no further adjustments should be necessary.

A cigarette is placed into each cigarette holder, through the access door 38, and lit as the smoking machine draws the first volume of air. The access door is closed and the cigarettes are allowed to burn to a predetermined length.

During the burning of the cigarette, mainstream smoke is intermittently drawn through the length of the cigarette to the smoking machine as it draws air through the cigarette holder. The mainstream smoke may be accumulated, collected, or filtered, as desired, provided that it is segregated from the sidestream smoke. The sidestream smoke will rise naturally from the cigarette firecone and accumulate in the upper portion 26 of the chamber means.

Once the cigarettes have burned to a predetermined length, an opacity reading may be taken directly from the meter M. As an alternative, the cigarette may be smoked a predetermined number of puffs. The number of cigarettes smoked per test may also vary, with any unused cigarette holders being plugged.

The opacity reading from the meter M may be converted to absorbance units as follows:

$$\text{absorbance} = 1/1 - \text{opacity}$$

Experimental data have indicated that the absorbance values are directly proportional to the amount of sidestream smoke within the sample chamber. To obtain absorbance values within an acceptable range one may modify the burned length of the cigarette, the number of cigarettes, or the length of the light path. Two cigarettes and a light path of approximately 6 inches were found to provide optimum values.

Following the burning of a set of cigarettes, the hinged portion 68 of the top cap 22 and the access door 38 may be opened to exhaust the smoke from the chamber in preparation for another test.

Although there are no universally recognized standards regarding the collection of sidestream smoke, and the foregoing experiments are based upon the assumption that sidestream smoke samples from different cigarettes affect light extinction in a similar manner, the results have been encouraging. For instance, no effort has been made to determine the effects, if any, of such influences as particle size, rate of coagulation, collection of particles on the chamber walls, gas phase components, composition, etc. However, because the test conditions are uniform for each sample, it is believed that any variable will be constant and the relative absorbance values obtained for different cigarettes should remain valid.

As with the alternate embodiments disclosed herein, it is apparent that this invention is capable of various modifications, especially to one having the benefit of the present disclosure. Accordingly, while the invention has been disclosed with reference to a preferred embodiment, it is to be understood that the disclosure is to be interpreted in its broadest sense and encompass the use of equivalent apparatus and mechanisms.

That which is claimed is:

1. A method of measuring the relative amount of sidestream smoke produced by a smoking material such as a cigarette, smoking tobacco or the like, said method comprising the steps of burning the smoking material to produce mainstream smoke and sidestream smoke;

segregating the sidestream smoke from the mainstream smoke and accumulating the segregated sidestream smoke produced from the burning smoking material; and measuring the relative amount of the accumulated sidestream smoke.

2. The method of claim 1 further comprising the initial step of confining the smoking material in an enclosure.

3. The method of claim 1 wherein the burning of the smoking material comprises the steps of igniting the smoking material and intermittently drawing air therethrough to simulate the smoking of a smoking material by a human.

4. The method of claim 1 wherein said mainstream smoke comprises smoke comingled with air drawn through said smoking material and said sidestream smoke comprises all other smoke produced by said smoking material when burned, wherein the step of burning the smoking material to produce mainstream smoke and sidestream smoke comprises intermittently drawing air through the burning smoking material.

5. The method of claim 4 wherein the step of segregating the sidestream smoke from the mainstream smoke comprises removing the drawn air and comingled mainstream smoke to a location remote from the smoking material while accumulating the sidestream smoke.

6. The method of claim 1 wherein the measuring of the relative amount of the accumulated sidestream smoke comprises the step of measuring the relative opacity thereof.

7. The method of claim 6 wherein the step of measuring the opacity of the accumulated sidestream smoke comprises transmitting light into the accumulated sidestream smoke; and sensing any attenuation of said transmitted light compared to its unattenuated intensity.

8. A method of measuring the relative amount of sidestream smoke produced by a smoking material such as a cigarette, smoking tobacco, or the like, said method comprising the steps of placing a smoking material into a smoking material holder located within an enclosure and having means for permitting air to be drawn through the smoking material;

igniting the smoking material;

obtaining mainstream smoke by intermittently drawing air through the ignited smoking material and withdrawing the mainstream smoke and drawn air from the enclosure;

obtaining sidestream smoke by accumulating in the enclosure all other smoke produced by the smoking material; and measuring the relative amount of the accumulated sidestream smoke.

9. The method of claim 8 wherein the smoking material comprises a cigarette and the smoking material holder comprises a tube that fits in an airtight relationship over the non-ignited end of the cigarette, and wherein the step of obtaining mainstream smoke comprises intermittently drawing air through the cigarette via the tube.

10. The method of claim 8 wherein the smoking material comprises a predetermined amount of smoking material and wherein the steps of obtaining mainstream smoke, withdrawing the mainstream smoke and drawn air, and obtaining sidestream smoke continue until the predetermined amount of smoking material has all burned.

11. The method of claim 8 wherein the step of measuring the relative amount of the accumulated sidestream smoke comprises the step of measuring the relative opacity thereof.

12. The method of claim 11 wherein the step of measuring the opacity of the accumulated sidestream smoke comprises transmitting light into the accumulated sidestream smoke; and sensing any attenuation of the transmitted light compared to its unattenuated intensity.

13. A method of measuring the relative amount of sidestream smoke produced by a cigarette, said method comprising the steps of confining the cigarette in an enclosure and placing one end of the cigarette into a cigarette holder having means for permitting air to be drawn through the length of the cigarette;

igniting the other end of the cigarette;

obtaining mainstream smoke by intermittently drawing air through the ignited cigarette and withdrawing the mainstream smoke from the enclosure;

obtaining sidestream smoke by accumulating all other smoke produced by the cigarette by permitting the other smoke to rise from the cigarette and collect in the enclosure; and measuring the relative opecity of the accumulated sidestream smoke.

14. The method of claim 13 wherein the step of measuring the relative opacity of the accumulated sidestream smoke comprises transmitting light into the accumulated sidestream smoke, sensing any attenuation of the transmitted light compared to its unattenuated intensity, and providing a signal proportional thereto.

15. Apparatus for measuring the relative amount of sidestream smoke produced by a burning smoking material such as a cigarette, smoking tobacco, or the like, said apparatus comprising means for holding the smoking material;

means for intermittently drawing air through said means for holding the smoking material and the smoking material to produce sidestream smoke and mainstream smoke, said mainstream smoke being comingled with the drawn air;

means associated with said means for holding the smoking material for collecting only the sidestream smoke from the smoking material and for accumulating the sidestream smoke; and means for measuring the relative amount of sidestream smoke in said means for collecting and accumulating.

16. The apparatus of claim 15 wherein said means for holding the smoking material comprises an annular collar defining an aperture through which air may be drawn and adapted to support the smoking material.

17. The apparatus of claim 15 wherein said means for collecting and accumulating the sidestream smoke comprises an enclosure associated with said means for holding the smoking material and placed above the smoking materials for receiving substantially all of said sidestream smoke rising from the smoking materials.

18. The apparatus of claim 15 wherein said apparatus for measuring the relative amount of the accumulated sidestream smoke comprises means for measuring the opacity of the accumulated sidestream smoke.

19. The apparatus of claim 18 wherein said means for measuring the opacity of the accumulated sidestream smoke comprises light transmitter means and light sensor means operatively associated for measuring the relative attenuation of light transmitted from said light transmitter means to said light sensor means and for providing a signal proportional thereto.

20. Apparatus for measuring the relative amount of sidestream smoke produced by a burning cigarette, said apparatus comprising
means defining an enclosure;
means located within the enclosure for holding at least one cigarette during the burning thereof;
means cooperating with the means for holding a cigarette for intermittently drawing air through a burning cigarette to produce sidestream smoke and mainstream smoke, the mainstream smoke being drawn through the length of a cigarette and comingled with the drawn air;
means for withdrawing the mainstream smoke from the enclosure while allowing the sidestream smoke to collect and accumulate within the enclosure; and
means for measuring the relative opacity of the accumulated sidestream smoke.

21. The apparatus of claim 20 wherein said means defining an enclosure further includes access means for permitting access to the means for holding a cigarette.

22. The apparatus of claim 20 wherein said means for holding a cigarette comprises an annular collar defining an aperture through which air may be drawn and adapted to support a cigarette from one end.

23. The apparatus of claim 20 wherein said means defining an enclosure further includes access means in the upper portion thereof for evacuating the enclosure.

24. The apparatus of claim 20 wherein said means defining an enclosure further defines at least one hole in the lower portion thereof for admitting outside air as mainstream smoke is withdrawn from the enclosure.

25. The apparatus of claim 20 wherein said means for measuring the relative opacity of the accumulated sidestream smoke comprises light transmitter means and light sensor means operatively associated for measuring the relative attenuation of light transmitted from said light transmitter means to said light sensor means and for providing a signal proportional thereto.

26. The apparatus of claim 25 wherein said means for measuring the relative opacity of the accumulated sidestream smoke further comprises a yoke having said light transmitter and light sensor attached to opposite, spaced ends thereof in a fixed, predetermined spatial relationship, said yoke being adapted to cooperate with said means defining an enclosure to direct therethrough the light from said light transmitter.

* * * * *